(12) United States Patent
Jones et al.

(10) Patent No.: US 7,951,092 B2
(45) Date of Patent: May 31, 2011

(54) GUIDEWIRE LOADER APPARATUS AND METHOD

(75) Inventors: Andrew Jones, San Jose, CA (US); Michael Zung, San Carlos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 807 days.

(21) Appl. No.: 11/418,692

(22) Filed: May 5, 2006

(65) Prior Publication Data
US 2006/0253048 A1 Nov. 9, 2006

Related U.S. Application Data

(60) Provisional application No. 60/678,145, filed on May 5, 2005.

(51) Int. Cl.
| | |
|---|---|
| *A61B 5/00* | (2006.01) |
| *A61B 6/00* | (2006.01) |
| *A61M 25/00* | (2006.01) |
| *A61M 25/16* | (2006.01) |
| *A61M 25/18* | (2006.01) |
| *A61M 39/00* | (2006.01) |
| *A61M 39/10* | (2006.01) |

(52) U.S. Cl. .................. 600/585; 600/434; 604/533
(58) Field of Classification Search .................. 600/585, 600/434; 606/528; 604/533
See application file for complete search history.

(56) References Cited

U.S. PATENT DOCUMENTS

| | | | | |
|---|---|---|---|---|
| 4,917,094 | A | * | 4/1990 | Lynch et al. ................... 600/434 |
| 5,191,888 | A | * | 3/1993 | Palmer et al. ................. 600/434 |
| 5,361,777 | A | * | 11/1994 | Sellers ........................... 600/585 |
| 5,439,012 | A | * | 8/1995 | D'Agostino .................... 132/73 |

(Continued)

FOREIGN PATENT DOCUMENTS

EP 0328760 8/1989

(Continued)

OTHER PUBLICATIONS

PCT patent application No. PCT/US2006/017750, International Search Report dated Oct. 6, 2006.

(Continued)

*Primary Examiner* — Max Hindenburg
*Assistant Examiner* — Sean P Dougherty
(74) *Attorney, Agent, or Firm* — Fulwider Patton LLP

(57) ABSTRACT

A guidewire loader apparatus is provided for loading a guidewire into a lumen opening of a guidewire lumen of a medical device. The loader apparatus includes a first member defining a respective medical device receiving portion and a respective guidewire receiving portion in communication therewith via a respective interface portion. The loader apparatus further includes a second member configured for placement in an opposed relationship to the first member. The second member defines a respective medical device receiving portion and a respective guidewire receiving portion in communication therewith at a respective interface portion. The first member and the second member cooperatively associate with one another between a first position and a second position. In the first position, the medical device can be positioned into at least one respective medical device receiving portion. In the second position, the respective device receiving portions cooperate to align and support the medical device in a manner placing the lumen opening of the medical device substantially adjacent to the cooperating, respective interface portions. This permits aligned sliding receipt of an end of the guidewire into the cooperating, respective guidewire receiving portions, through the cooperating respective interface portions and into the lumen opening of the medical device.

13 Claims, 8 Drawing Sheets

U.S. PATENT DOCUMENTS

| | | | |
|---|---|---|---|
| 5,651,373 A * | 7/1997 | Mah | 600/585 |
| 5,830,157 A * | 11/1998 | Foote | 600/585 |
| 5,978,699 A * | 11/1999 | Fehse et al. | 600/434 |
| 6,190,333 B1 * | 2/2001 | Valencia | 600/585 |
| 6,551,281 B1 * | 4/2003 | Raulerson et al. | 604/164.13 |
| 6,869,417 B1 | 3/2005 | Walters et al. | |
| 6,879,854 B2 | 4/2005 | Windheuser et al. | |
| D561,896 S * | 2/2008 | Jones | D24/130 |
| 7,713,261 B2 * | 5/2010 | Nash et al. | 604/533 |
| 2004/0059369 A1 | 3/2004 | Duffy et al. | |
| 2005/0178684 A1 * | 8/2005 | Kesler et al. | 206/364 |
| 2006/0253048 A1 * | 11/2006 | Jones et al. | 600/585 |

FOREIGN PATENT DOCUMENTS

| | | |
|---|---|---|
| EP | 0801955 A1 | 10/1997 |
| FR | 2804608 | 8/2001 |

OTHER PUBLICATIONS

PCT patent application No. PCT/US2006/017750, Written Opinion dated Oct. 6, 2006.

* cited by examiner

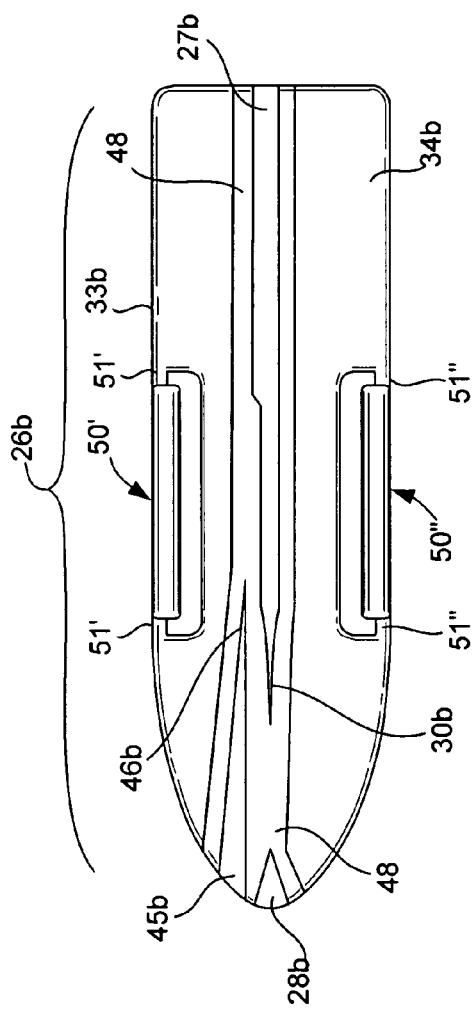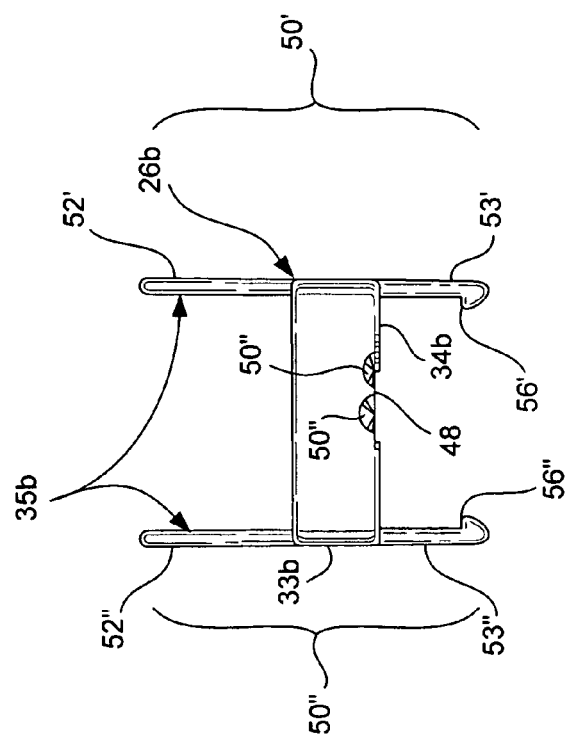

GUIDEWIRE LOADER APPARATUS AND METHOD

RELATED APPLICATION DATA

The present application claims priority under 35 U.S.C. §119 to U.S. Provisional Application Ser. No. 60/678,145, naming Zung as the inventor, filed May 5, 2005, and entitled GUIDEWIRE LOADER, the entirety of which is incorporated herein by reference for all purposes.

FIELD OF THE INVENTION

The present invention relates to medical devices in general, and in particular to a device for facilitating the loading of guidewires into medical devices.

BACKGROUND OF THE INVENTION

As an alternative to invasive-type surgeries whereby a physician creates an incision to access a desired location in the patient's body, many minimally invasive surgeries and in vivo examinations are being performed using catheters that are inserted into a patient's body. With a catheter in place, medical devices are routed through a lumen in the catheter in order to obtain tissue samples, perform a surgical procedure or diagnose tissue in a patient's body.

To insert a catheter, many physicians first use a guidewire that is routed to a desired location in the patient's body. The guidewire then acts as a rail over which catheters or other medical devices can be easily routed to the desired location.

Typically medical devices for insertion within a patient have a guidewire lumen extending through at least a portion thereof. Generally, the guidewire lumen is sufficiently sized to allow the device to pass over the guidewire freely. General diameters for guidewires are 0.014 to 0.038 inches, therefore the corresponding guidewire lumen must be sized accordingly.

To route a medical device over the guidewire, the guidewire must be inserted into a guidewire lumen of the medical device. Routing the guidewire into the guidewire lumen proves to be difficult for many reasons. For example, many times the tip of the catheter is formed having a curved shape wherein the guidewire lumen is coaxially disposed within the curve. Therefore, in order to dispose the guidewire into the lumen, the operator must straighten the curled tip of the catheter while simultaneously inserting the guidewire. This process may be further complicated by coatings applied to either the guidewire or the catheter, or both, which may make the surfaces slippery thereby hindering the process.

Further still, many modern guidewires include tips of differing flexibilities at their proximal and distal ends, thereby giving the physician the option of adjusting the flexibility depending on which end of the guidewire is inserted into the patient. However, such flexible tips are difficult to use with catheters because they are not stiff enough to be easily disposed within the guidewire lumen without severely bending and possibly kinking the catheter. Therefore, there is a need for a device that helps align and load a guidewire into a guidewire lumen of a medical device.

SUMMARY OF THE INVENTION

To address the above-mentioned problems, the present invention provides a tool for aligning and facilitating insertion of a guidewire into a guidewire lumen of a medical device. The tool includes a handle having a portion sized to receive a medical device therein and a lumen aligned with the medical device receiving portion to direct a guidewire into a lumen. The lumen may further include a tapered portion on each end to ease engagement of the medical device and the guidewire.

In one exemplary embodiment of the invention there is provided a guidewire loader, comprising a first member and a second member, the first and second members are spaced apart and connected about a hinge member. Each member further includes a medical device receiving portion and a guidewire receiving portion adjacent the hinge member.

In another specific embodiment, a guidewire loader apparatus is provided for loading a guidewire into a lumen opening of a guidewire lumen of a medical device. The loader apparatus includes a first member defining a respective medical device receiving portion and a respective guidewire receiving portion that terminates at the device receiving portion at a respective interface portion. The loader apparatus further includes a second member configured for placement in an opposed relationship to the first member. The second member defines a respective medical device receiving portion and a respective guidewire receiving portion in communication therewith at a respective interface portion. The first member and the second member cooperatively associate with one another between a first position and a second position. In the first position, the medical device can be positioned into at least one respective medical device receiving portion. In the second position, the respective device receiving portions cooperate to align and support the medical device in a manner placing the lumen opening of the medical device substantially adjacent the cooperating, respective interface portions. This permits aligned sliding receipt of an end of the guidewire into the cooperating, respective guidewire receiving portions, through the cooperating respective interface portions and into the lumen opening of the medical device.

In one particular configuration, each respective guidewire receiving portion is semi-conical-shaped, tapering inwardly toward the respective interface portion. Further, each respective medical device receiving portion is semi-cylindrical-shaped.

Each the first member and the second member include a respective base portion configured for placement in an opposed relationship to one another. Each respective base portion defines the respective device receiving portion, the guidewire receiving portion and the interface portion. A respective manipulating tab is provided to enable manual operation between the first position and the second position.

In one specific embodiment, each respective manipulating tab is configured for placement in opposed relationship to one another, and extend radially away from an longitudinal axis of the respective device receiving portion. The loader apparatus further includes a hinge portion hingeably mounting the first member to the second member for clamshell movement of the respective base portions between the first position and the second position.

Another specific arrangement provides a manipulating tab of the second member that includes a pair of opposed clip members hingeably mounted to the respective base portion on opposed sides of a longitudinal axis of the respective medical device receiving portion. One end of each clip member contains a respective grip portion, and an opposite end thereof contains a clip portion configured to releasably grip a corresponding clip region of the first member when the loader apparatus is in the second position.

In still another specific configuration, each the first member and the second member have a substantially planar engaging face in opposed relationship with one another in the second position. Each engaging face defines the respective medical device receiving portion, the respective guidewire receiving portion and the respective interface portion.

Another specific configuration includes alignment structure which cooperates between the first member and the second member to align the respective medical device receiving portions, the guidewire receiving portions and the interface portions with one another, when the first and second member are oriented in the second position. In one embodiment, the alignment structure includes an alignment lip upstanding from one of the engaging faces, and peripherally surrounding at least a portion of the respective medical device receiving portion, the guidewire receiving portion and the interface portion. The alignment structure further includes a corresponding alignment recess downstanding from the other of the engaging faces, and peripherally surrounding the other of the at least a portion of the respective medical device receiving portion, the guidewire receiving portion and the interface portion.

In another specific embodiment, the first member further defines a respective second guidewire receiving portion in communication therewith at a respective second interface portion. The second member further defines a respective second guidewire receiving portion in communication therewith at a respective second interface portion. In the second position, the respective device receiving portions cooperate to align and support the medical device in a manner placing a second lumen opening of a second guidewire lumen of the medical device substantially adjacent the cooperating, respective second interface portions. This permits aligned sliding receipt of an end of a second guidewire into the cooperating, respective second guidewire receiving portions, through the cooperating, respective second interface portions and into the second opening of the second guidewire lumen of the medical device.

Each respective guidewire receiving portion and second guidewire receiving portion is semi-conical-shaped, tapering inwardly toward the respective interface portion, and each respective medical device receiving portion is semi-cylindrical shaped. In one embodiment of the guidewire loader, the first and second members have respective cavities that define catheter receiving portions. The first and second elements may also be clamped together by mirror image clips on opposite sides of the first and second members. The first and second elements or portions thereof may be made from transparent material. In still another embodiment, the interface portion includes smooth interiors without a stepped transition, and optionally a manipulating tab extends from the respective base portion in a direction generally parallel to the longitudinal axis of the loader and catheter.

In another aspect of the present invention, a method is provided for loading a guidewire into a lumen opening of a guidewire lumen of a medical device. The method includes orienting at least one of a first member and a second member in a first position, enabling access to a respective engaging face of the at least one of the first member and the second member. The engaging face defines a respective medical device receiving portion and a respective guidewire receiving portion in communication therewith at a respective interface portion. In the first positioned, loading the medical device into a respective medical device receiving portion of the at least one first member and second member in a manner positioning the lumen opening thereof substantially adjacent the respective interface portion. The method further includes gripping and aligning the medical device between the first member and second member, in a second position. In this position, the first and second members are oriented in opposed relationship to one another such that the opposed guidewire receiving portions collectively form a guidewire receiving feature. Similarly, the opposed medical device receiving portions collectively form a medical device receiving feature that cooperatively aligns and supports the lumen opening of the medical device substantially adjacent the cooperating, respective interface portions. Next, the method includes inserting an end of the guidewire into the guidewire receiving feature, through the cooperating, respective interface portions and into the lumen opening of the medical device

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIG. 8 is a bottom plan view of a second member of the guidewire loading apparatus of FIG. 4.

FIG. 9 is a front elevation view of the second member of FIG. 8.

DETAILED DESCRIPTION

Figure 1:
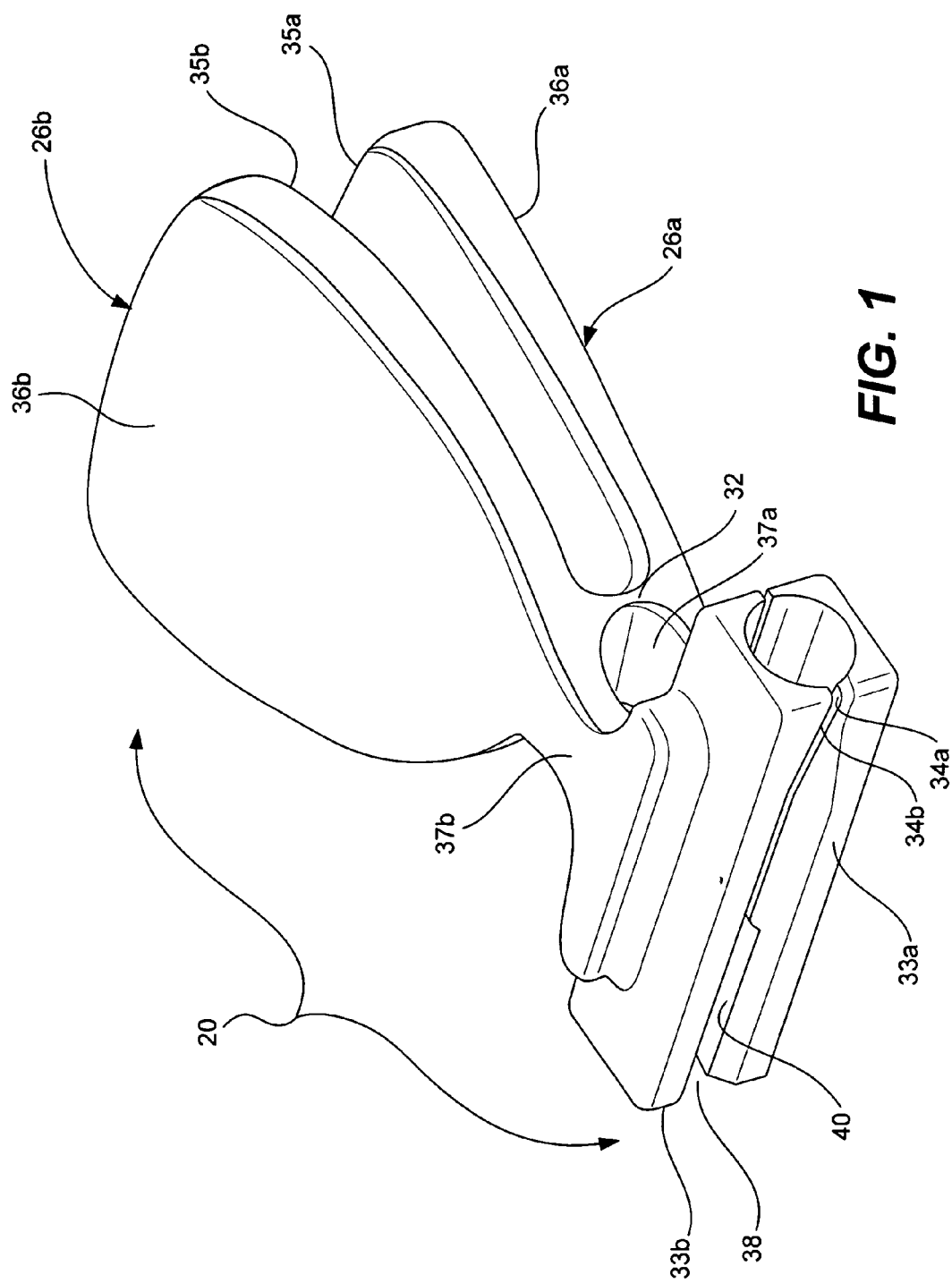
FIG. 1 is a top perspective view of a guidewire loading apparatus in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 2:
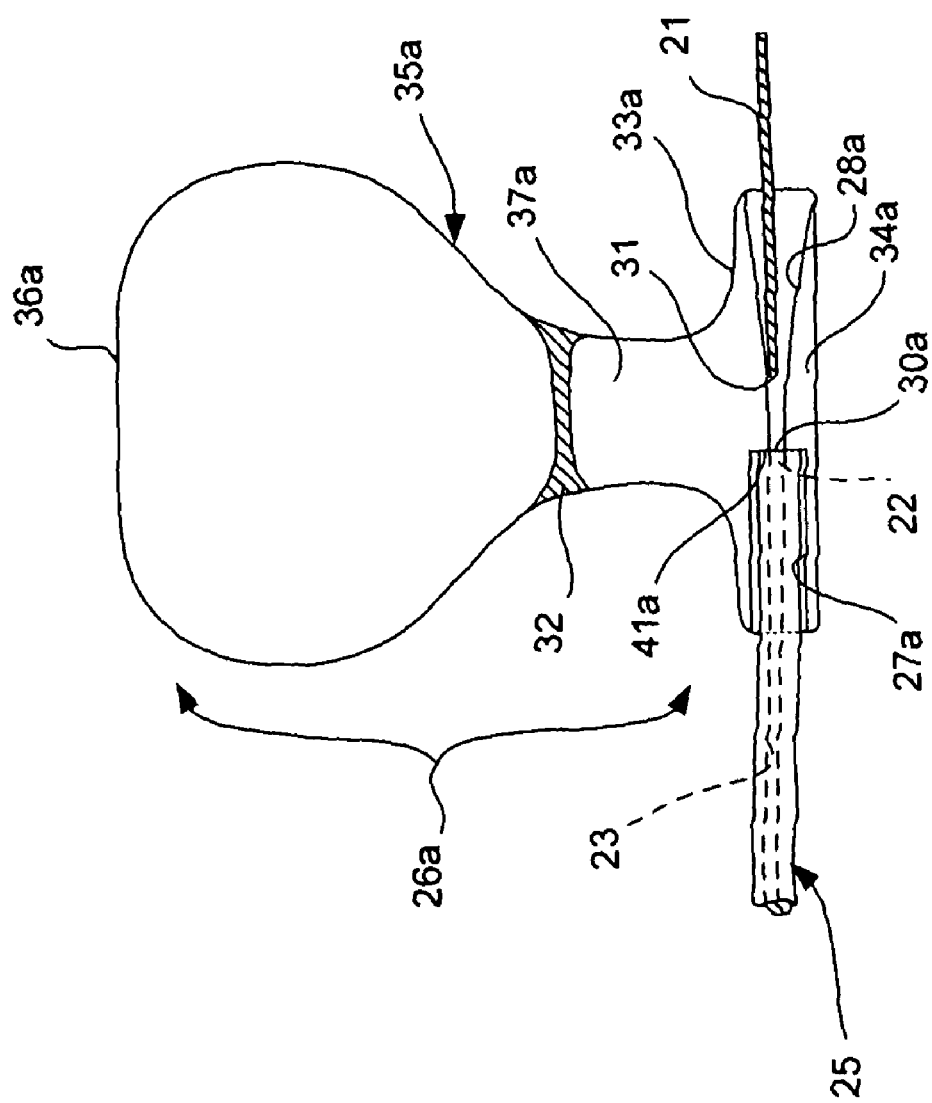
FIG. 2 is a reduced top plan view, in cross-section, of a member of the guidewire loader apparatus of FIG. 1, illustrating insertion of a guidewire into a medical device loaded in a medical device receiving feature of the apparatus.
Figure 3:
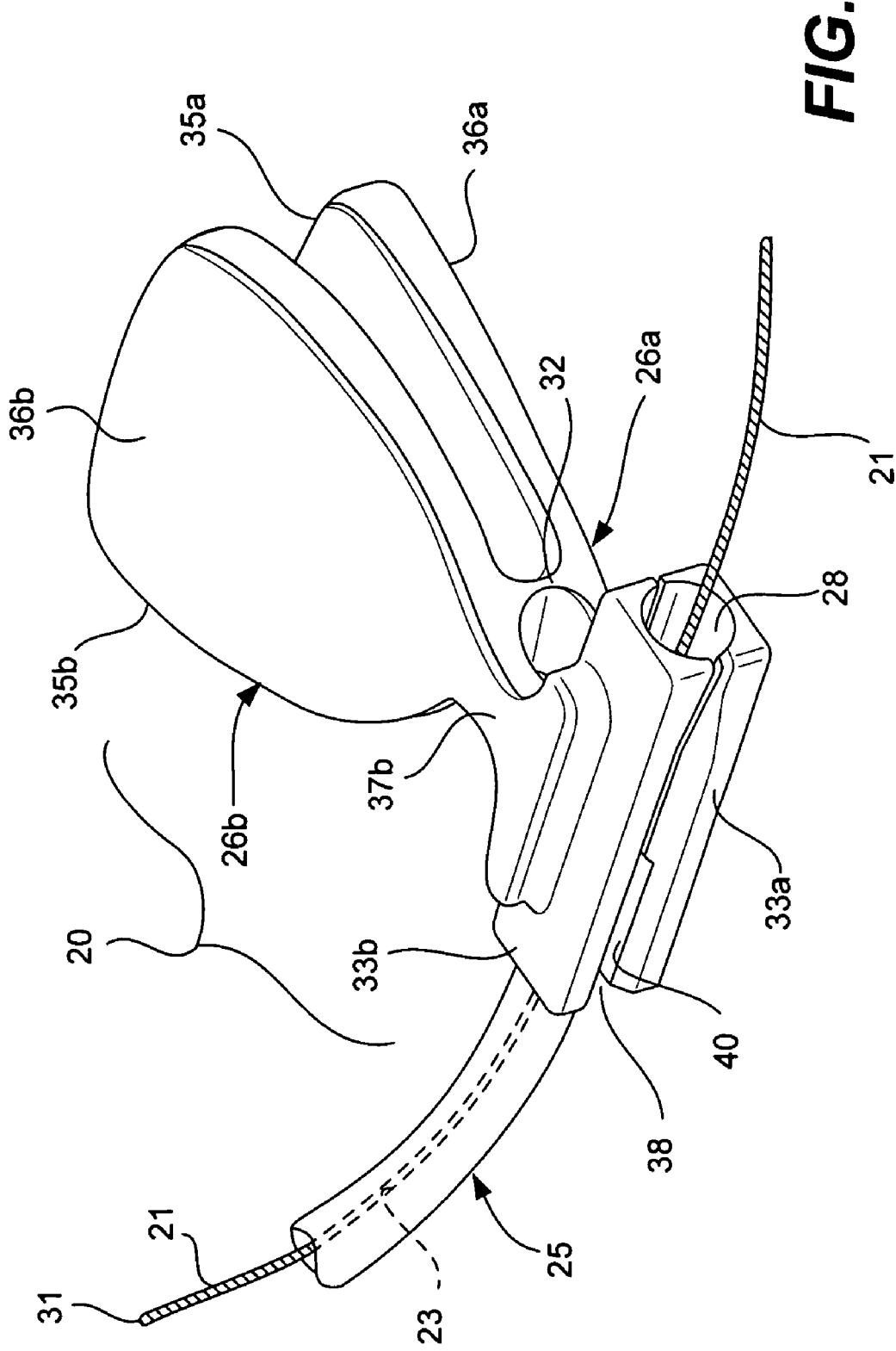
FIG. 3 is a reduced top perspective view of the guidewire loading apparatus of FIG. 1, as disposed on the distal end of a medical device and configured to receive a guidewire therein.
Figure 4:
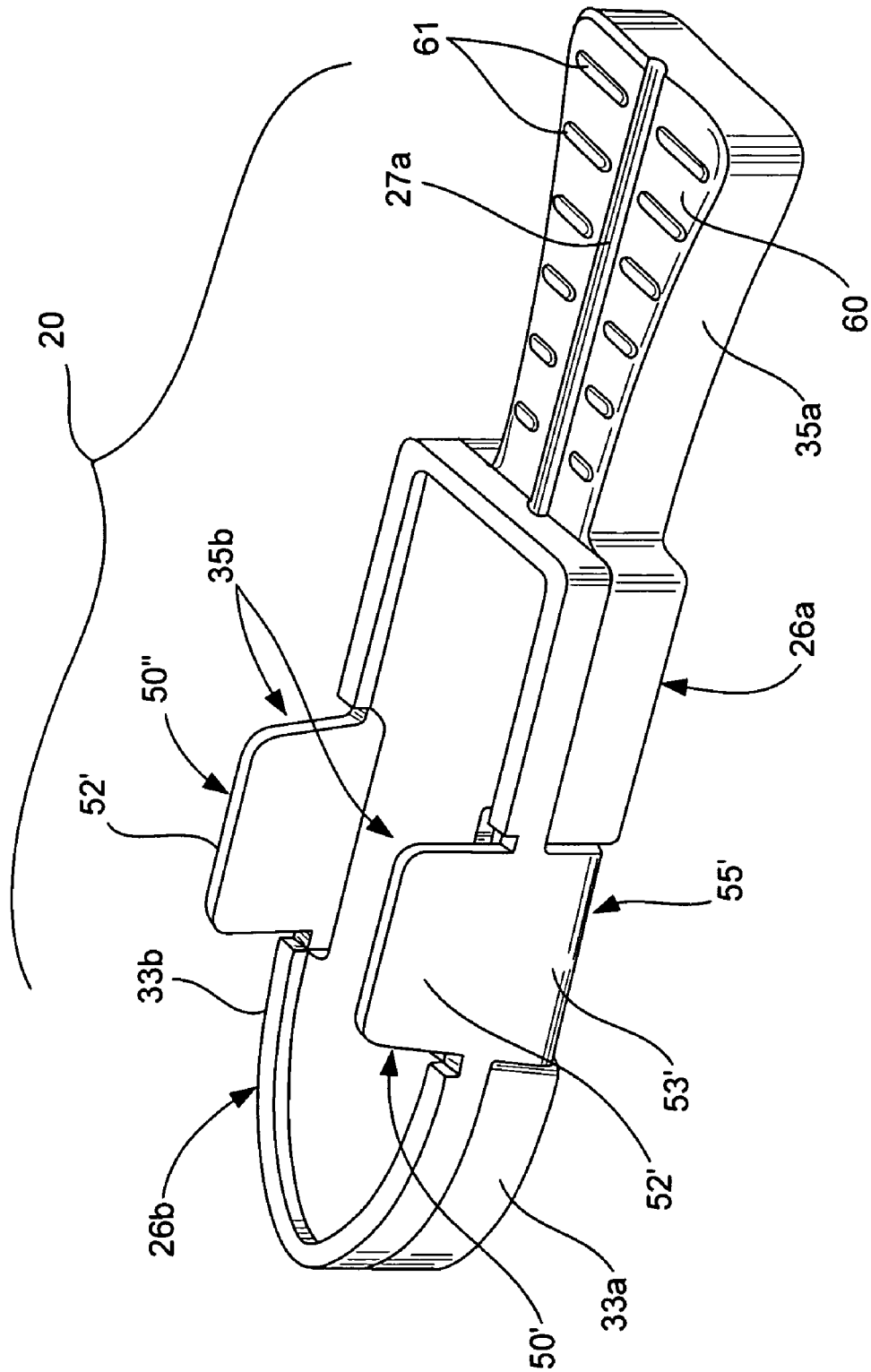
FIG. 4 is a top perspective view of an alternative embodiment guidewire loading apparatus in accordance with the present invention, shown in a second position.
Figure 5:
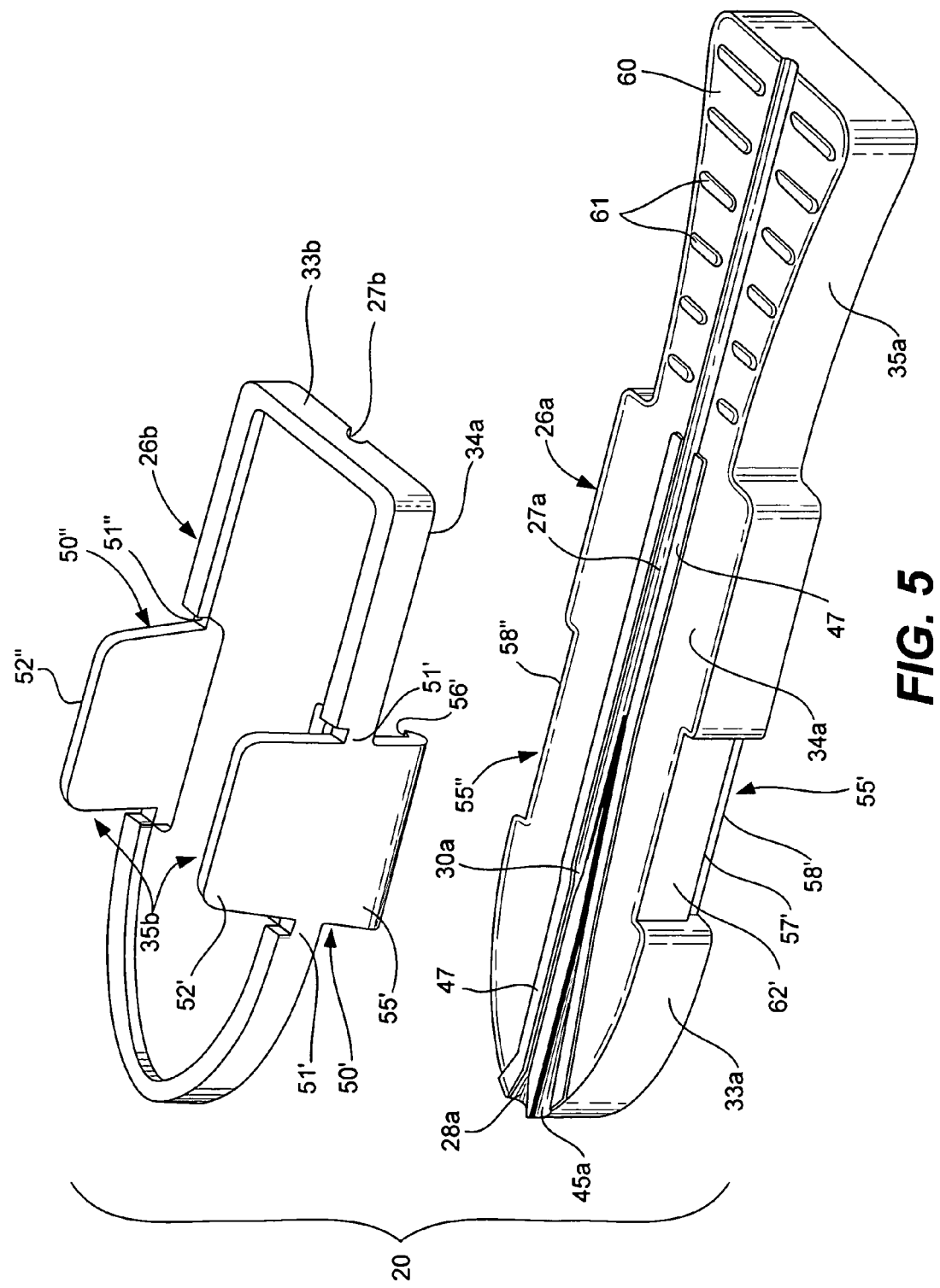
FIG. 5 is a top perspective view of the guidewire loading apparatus of FIG. 4, illustrating a first position.
Figure 6:
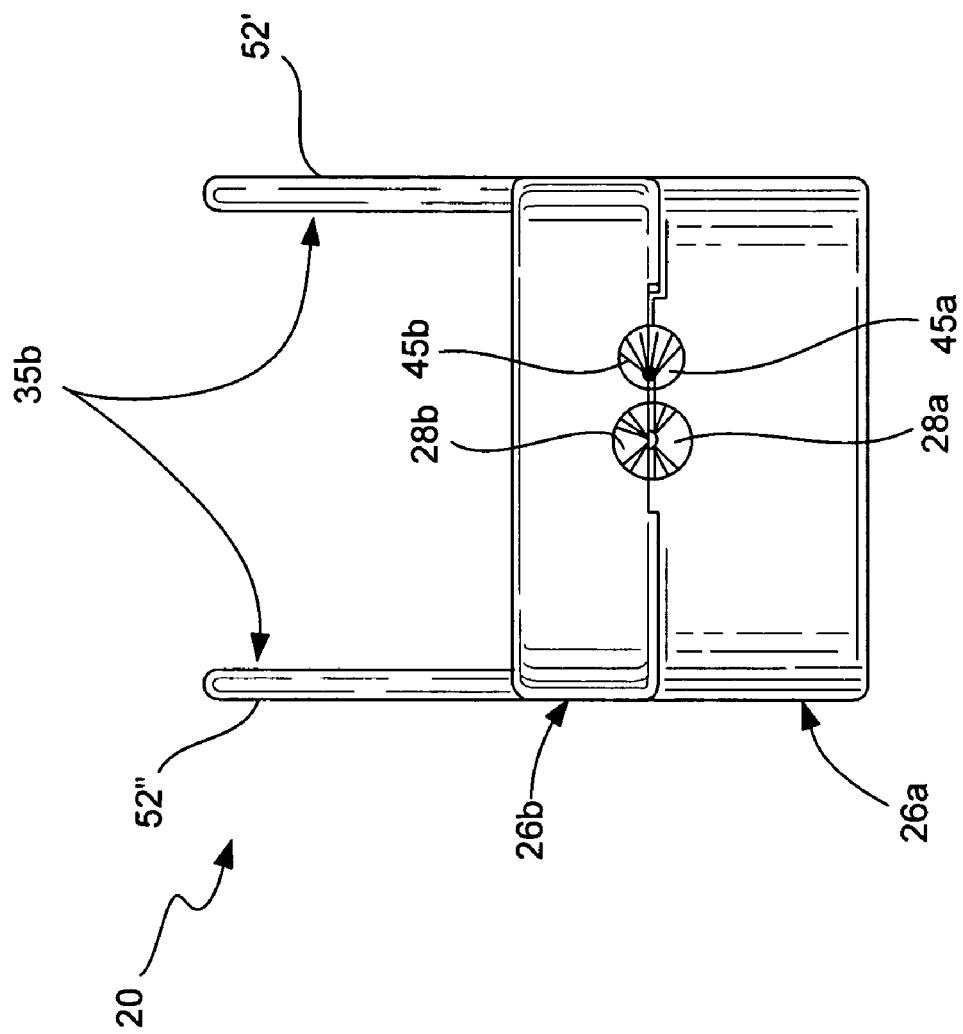
FIG. 6 is a front elevation view of the guidewire loading apparatus of FIG. 4.
Figure 7:
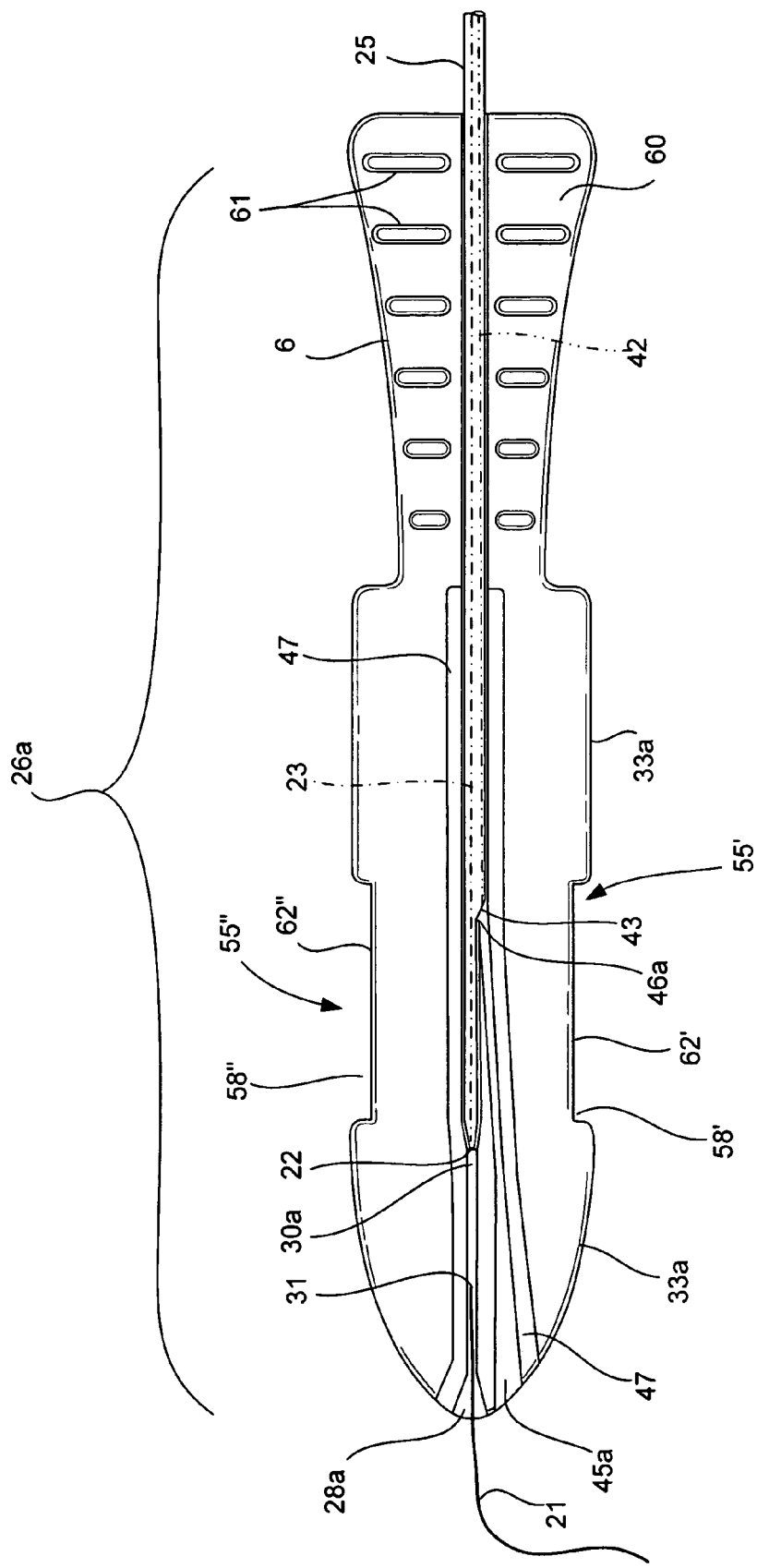
FIG. 7 is a bottom plan view of a first member of the guidewire loading apparatus of FIG. 4.

Referring now to a first embodiment of FIGS. 1-3 and a second embodiment of FIGS. 4-7, a guidewire loader apparatus, generally designated 20, is provided for loading a guidewire 21 into a first lumen opening 22 of a first guidewire lumen 23 of a medical device 25. The guidewire loader apparatus 20 includes a first member 26*a* defining a respective medical device receiving portion 27*a* and a respective first guidewire receiving portion 28*a* in communication therewith via a respective first interface portion 30*a* (FIGS. 2 and 7). A second member 26*b* is also provided that is configured for placement in an opposed relationship to the first member 26*a* (FIGS. 1 and 4). The second member 26*b* defines a respective medical device receiving portion 27b and a respective first guidewire receiving portion 28b in communication therewith at a respective first interface portion 30b (FIG. 8).

The first member 26a and the second member 26b cooperatively associate with one another between a first position (FIGS. 2 and 5) and a second position (FIGS. 3 and 4). In the first position, the medical device 25 can be positioned into at least one respective medical device receiving portion 27a or 27b. In the second position, the respective device receiving portions 27a, 27b cooperate to align and support the medical device 25 in a manner placing the first lumen opening 22 thereof substantially adjacent the cooperating, respective first interface portions 30a, 30b (as shown in the cross-section of FIGS. 2 and 7). This permits aligned sliding receipt of a distal end 31 of the first guidewire 21 into the cooperating, respective first guidewire receiving portions 28a, 28b, through the cooperating, respective first interface portions 30a, 30b and into the first lumen opening 22 of the medical device 25.

Accordingly, the present invention guidewire loader apparatus provides a simple, effective technique to load an end of a guidewire into the minute openings of a guidewire lumen of a medical device. This efficient technique enables precision loading without the need for any manual handling or the sterile devices supported on the end of a medical device, such as a crimped stent. Moreover, the present invention may be disposed or pre-loaded on an end of a suitable medical device, prior to packaging and sterilization, or the guidewire loader apparatus can be included in the packaging with the medical device prior to sterilization.

Referring now to FIG. 1, there is shown an exemplary embodiment of a guidewire loader apparatus 20 in accordance with the present invention. The guidewire loader apparatus 20 includes first and second members 26a, 26b connected through a hinge member 32 in an opposed relationship to one another. Each first and second member 26a, 26b includes a generally elongated base portion 33a, 33b and a respective manipulating tab 35a, 35b extending generally outward in a direction radially away from a longitudinal axis of the respective base portion. In this configuration, manipulation of the opposed manipulating tabs 35a, 35b, hinged about hinge member 32, enable selective clam-shell movement operation of the opposing base portions 33a, 33b between the first position (spreading the opposed base portions 33a, 33b apart to facilitate side loading of a medical device therein as shown in FIG. 2) and the second position (FIGS. 1 and 3), which will be described in greater detail below.

In this specific embodiment, each member 26a, 26b is substantially the mirror image of one another. Hence, while the guide wire receiving portion and the medical device receiving portion of the second member 26b are not shown, it will be appreciated that these components are essentially an identical mirror-image of the corresponding receiving portions of the first member 26a, shown in FIG. 2. Thus, turning now to FIG. 2, the respective base portion 33a defines a substantially planar engaging face 34a. When the base portions 33a, 33b are in the second position, the two substantially planar opposed engaging faces 34a, 34b are oriented in a substantially opposed relationship to one another (FIGS. 1). FIG. 2 illustrates that engaging face 34a defines a respective device receiving portion 27a and a respective first guidewire receiving portion 28a. These receiving portions are respectively substantially co-axially aligned with one another, and intercommunicate via the corresponding first interface portion 30a. In particular, the respective first interface portion 30a interconnects an end of the respective device receiving portion 27a with the corresponding distal end of the respective first guidewire receiving portion 28a.

As illustrated, the device receiving portion 27a is generally semi-cylindrical-shaped, and is sized to receive a number of medical devices having different diameters, such as a delivery catheter. When the loader apparatus 20 is oriented in the second position (FIGS. 1 and 3), two opposed medical device receiving portions 27a, 27b of the opposed base portions 33a, 33b collectively cooperate to define a substantially cylindrical medical device receiving feature particularly suitable for receipt of a catheter device therein.

Referring now to the guidewire receiving feature of each base portion 33a, 33b, the respective guidewire receiving portion 28a is preferably semi-conical shaped, tapering from a larger radius at a proximal end to a smaller radius at a distal end (FIG. 2). The smaller radius at a distal portion of the guidewire receiving portion 28 is sized to substantially match radius of the first interface portion 30a. It will be appreciated, of course, that diameter or transverse cross-sectional dimension of the interface is sufficient for sliding receipt of the selected guidewire therethrough. Collectively, these two semi-conical shaped receiving portions 28, in the second position, cooperate to form a conical-shaped guidewire receiving feature. Hence, the gradual taper facilitates receipt, alignment and guidance of a guidewire into a properly positioned medical device.

Referring now to FIGS. 1 and 3, the opposed manipulating tabs 35a, 35b are illustrated having butterfly wing-shaped gripping bodies 36a, 36b that taper inwardly towards respective neck portions 37a, 37b that connect to the respective base portions 33a, 33b. The tabs 35a, 35b are hingeably coupled together via a hinge member 32 preferably positioned at an intersection between the gripping bodies 36a, 36b and the corresponding neck portions 37a, 37b. Depending upon the selected length of the neck portions 37a, 37b, the clamshell movement displacement between the opposed engaging faces 36a, 36b of the corresponding base portions 33a, 33b, in the first position, can be adjusted. Accordingly, the guidewire loader apparatus 20 is constructed as a unitary member, wherein the hinge member 32 couples the two members together. Additionally, it is contemplated that each the first member 26a and the second member 26b could includes independent hinge member 32 that are coupled together to form mating units as well.

In one specific configuration, the guidewire loader apparatus 20 is injection molded as a single unit. Preferably, the material composition is substantially rigid, yet sufficiently resilient, at least at the hinge member 32. In this configuration, the hinge members bias the first and second members 26a, 26b toward the second position (FIGS. 1 and 3). It is contemplated, however, that the present invention may be constructed in other manners, such as multiple components that could then be assembled to form the guidewire loader in accordance with the present invention. Examples of suitable materials include a combination of over-molded polycarbonate and polyurethane plastics. In one embodiment, the upper second member 26b is composed of a clear polycarbonate to help the cardiologist thread the catheter into the stent, while the lower first member 26a is composed of an over-mold combination of polycarbonate and polyurethane to keep the stent in place.

In operation, referring now to FIG. 3, there is shown the guidewire loader apparatus 20 is shown disposed on the distal end of a medical device 25. To load the guidewire loader apparatus, a compression force is to the opposed gripping bodies 36a, 36b of the corresponding manipulation tabs 35a, 35b, causing the opposed base portions 33a, 33b to pivot about the hinge member 32. By depressing the gripping portions closer together, the displacement between the two opposed engaging faces 36a, 36b can be increased, in the first position. This spacing permits the distal end of a medical device 25 to be easily received and positioned within at least one of the device receiving portions 27a, 27b.

To accommodate side entry of the device into a mouth opening 38 formed between the sides of the pivoting base portions 33a, 33b, at least one of the base portions provides a recessed ledge portion 40 adjacent the respective device receiving portion 27. Since these recessed ledge portions 40 facilitate side entry clearance, the overall pivotal displacement of the base portions 33a, 33b necessary to receive the device can be reduced.

As best viewed in FIG. 2, the end of the medical device 25 is positioned such that the first lumen opening 22 into the first lumen 23 is oriented adjacent the first interface portion 30. This is performed by placing the end of the medical device in or near abutting contact against an end shoulder 41 of the device receiving portion 27. In this configuration, rotational alignment of the medical device about a longitudinal axis thereof, relative to the device receiving portion 27 is not necessary.

Once the medical device is properly positioned, the force applied to the gripping bodies 36a, 36b is removed, allowing the opposed base portions 33a, 33b to move together toward the second position (FIG. 3), via the resiliency of the hinge member 32. As illustrated in FIG. 2, the medical device 25 is secured and supported within the respective device receiving feature collectively formed between the respective device receiving portions 27a, 27b.

The distal end 31 of the guidewire 21 may then be inserted into the opening of the guidewire receiving portion 28, wherein the conical shape of the guidewire receiving portion urges the distal end 31 of the guidewire 21 toward and into the first interface portion 30 (FIG. 2). Further advancement causes the distal end 31 to align with the lumen opening 22 until the guidewire passes into the guidewire lumen 23 of the medical device (FIG. 3).

After the distal end of the guidewire 21 has been inserted into the medical device 25, the guidewire loader may be removed from the end of the medical device 25 by applying a similar inward force to the opposed manipulating tab gripping bodies 36a, 36b. Consequently, the base portions 33a, 33b are spread apart in the clam-shell movement by an amount sufficient to release the medical device 25 with the loaded guidewire. This is particularly useful since side removal between the clam-shell movements of the base portions need not require stringing the loader all the way down the guidewire 21 to a proximal end thereof.

Referring now to FIGS. 4-9, an alternative embodiment of the guidewire loader apparatus 20 is provided that is capable of loading medical devices supporting two guidewires, such as bifurcation stent delivery catheters. In these dual guidewire medical devices, a second guidewire lumen 42 is disposed adjacent the first guidewire lumen 23. Generally, however, a second lumen opening 43 into the second guidewire lumen 42 may be positioned proximal to the first lumen opening.

Accordingly, in this dual configuration, the respective engaging faces 36a, 36b of the corresponding base portions 33a, 33b will further define a respective second guidewire receiving portion 45a (FIG. 7) and 45b (FIG. 8) that terminates at the respective medical device receiving portions 27a, 27b at respective second interface portions 46a, 46b. The longitudinal position and placement of the respective second interface portions 46a, 46b, thus, must suitably match the longitudinal position of the second lumen opening 43 of the medical device 25.

Referring now to FIGS. 5 and 7, the respective second guidewire receiving portions 45a, 45b are preferably semi-conical shaped, similar to the respective first guidewire receiving portions 28a, 28b. Hence, the cooperating second guide receiving portions taper inwardly from a larger radius at a proximal end to a smaller radius at a distal end thereof. Again, the smaller radius is sized to substantially match radius of the second interface portion 46a, 46b.

In one specific embodiment, while the respective first and second guidewire receiving portions 28a, 28xb, and 45a, 45b, the respective first and second interface portions 30a, 30b, and 46a, 46b, and the respective device receiving portions 27a, 27b, collectively form the two guidewire receiving features and the medical device receiving feature, they need not be identical mirror images of one another. In fact, due to the nature an alignment structure, to be henceforth, one base portion 33 may define a more significant section of the collective receiving feature than that of the other base portion (FIGS. 7 and 8).

In accordance with the present invention, alignment structure may be incorporated to facilitate precision alignment between the opposed, respective medical device receiving portions 27a, 27b, the first and second guidewire receiving portions 28a, 28b and 45a, 45b, and the interface portions 30a, 30b and 46a, 46b when the first and second members 26a, 26b are oriented in the second position (FIGS. 4 and 6). The alignment structure may include an alignment lip 47 upstanding from one of the engaging faces (e.g., face 34a of the first member 26a). Further, the other engaging face (e.g., face 34b of the second member 26b) may define a corresponding alignment recess 48 downstanding therefrom that is aligned and sized for receipt of the upstanding alignment lip 47, when the opposed engaging faces 36a, 36b, and thus the first member and second member, are oriented in the second position. These mating alignment components facilitate precision alignment between the opposed respective medical device receiving portions, the guidewire receiving portions and the interface portions, in the second position.

More preferably, as best viewed in FIGS. 5 and 7, the upstanding alignment lip 47 peripherally surrounds at least a portion of one of the respective medical device receiving portion 27a, the first and second guidewire receiving portion 28a, 45a and/or the first and second interface portions 30a, 46a. Similarly, the corresponding alignment recess 48 (FIGS. 8 and 9), in this configuration, also peripherally surrounds the other of the at least a portion of the respective medical device receiving portion 27b, the first and second guidewire receiving portion 28b, 45b and/or the first and second interface portions 30b, 46b. It will be appreciated of course that while the first member 26a is shown and described as defining the upstanding alignment lip 47, it could have just as easily defined the downstanding alignment recess 48 as well, or a combination thereof, without departing from the true spirit and nature of the present invention.

To further align and retain the opposed base portions 33a, 33b of the corresponding first and second members 26a, 26b securely to one another, in the second position, an analogous manipulating tab 35b may be provided in the form of a pair of opposed clip members 50', 50" (FIG. 9). In one specific embodiment, these opposed clip members 50', 50" are hingeably mounted (at hinged sections 51', 51" that flank the clip members) to the respective base portion (e.g., base portion 33b in FIGS. 8 and 9) on opposed sides of a longitudinal axis of the respective medical device receiving portion 27b. Again it will be appreciated that the clip members 50', 50' can also be easily provided by the first member 26a as well.

One end of each clip member 50', 50" contains a respective grip portion 52', 52" (FIGS. 4, 6 and 9), while an opposite end thereof contains a clip portion 53', 53" configured to releasably grip and engage a corresponding clip region 55', 55" of the opposed base portion 33a of the first member 26a when the loader apparatus is in the second position. Preferably, grip portions 52', 52" (FIG. 4) are generally parallel to the longitudinal axis of the medical device receiving portion 27a. More preferably, each clip portion 53', 53" includes a respective ting 56', 56" (FIGS. 5 and 9), while the corresponding clip region 55', 55" is provided by a shoulder portion 57', 57" (FIG. 5) that cooperate with the corresponding tings to retain the first and second members in the second position. The opposed clip portions 53', 53" (e.g., tings) of the second member 26b are sized, dimensioned and spaced to engage the corresponding clip regions 55', 55" (e.g., shoulder portions) of the first member 26a. Each clip region 55', 55" includes spaced-apart clip slots 58', 58" sized and dimensioned for receipt of the corresponding clip portions 53', 53" during assembly from the first position to the second position.

Referring now to FIGS. 4, 5 and 7, the first member 26a also includes an analogous manipulating tab 35a that extends proximally from the respective base portion 33a, in a direction generally along the longitudinal axis of the respective medical device receiving portion 27. The tab 35 includes an upward facing surface 60 containing a plurality of laterally extending gripping ribs 61. The ribs 61 and the manipulating tab 35 enables gripping of the first member 26a, and is particularly functional when loading the medical device 25 in the corresponding device receiving portion 27a. In fact, a portion of the respective medical device receiving portion 27a extends continuously along the upward facing surface 60 of the manipulating tab 35a.

Accordingly, in the first position (FIGS. 5 and 7), the dual guidewire lumen medical device 25 may be loaded onto the first member 26a. Initially, the medical device 25 is aligned with and placed into the respective device receiving portion 27a of the corresponding base portion 33 of the first member 26a. As shown in FIG. 7, the distal tip of the medical device is placed proximate to the first interface portion 30a, orienting the first lumen opening 22 adjacent the same. Further, the medical device 25 is rotated about its longitudinal axis in an effort to align the second interface portion 46a adjacent to the second first lumen opening 22 of the medical device. Once properly oriented and positioned, the user may grip the manipulating tab 35a and a portion of the loaded medical device 25 together, sandwiching and securing the medical device 25 between their thumb or finger and the upward facing surface 60 just prior to assembly of the first and second members 26a, 26b.

The second member 26b is then aligned with the first member 26a, as shown in (FIG. 5), by initially placing the opposed engaging faces toward one another. To assemble the first and second members, the clip portions 53', 53" of the clip members 50', 50" are align with the clip slots 58', 58" of the second member base portion 33b. As the opposed base portions 33a, 33b are forced together, a backside ramp surface of the corresponding clip portion 53', 53" slideably engages and contacts a corresponding sidewall 62', 62" defining the clip slots 58', 58", causing resilient movement of the clip members 50', 50" about the corresponding hinged sections 51', 51". Once the corresponding tings 56', 56" move beyond an edge of the shoulder portions 57', 57" of the clip region 55', 55", the first and second members 26a, 26b are releasably retained together, as well as securing the medical device 25 in the second position (FIGS. 4 and 6).

FIG. 7 best illustrates that once the medical device 25 is properly positioned, a distal end of a guidewire (e.g., guidewire 21) may be inserted into either opening of the first guidewire receiving portion 28a or the second guidewire receiving portion 45a. The respective conical shape of either guidewire receiving portion urges the distal end of the guidewire 21 toward and into the first interface portion 30 or the second communication portion, respectively. Further advancement causes the distal end to align with the first lumen opening 22 or second lumen opening of the medical device until the guidewire passes into the first guidewire lumen 23 of the second guidewire lumen thereof.

After insertion of one or both guidewires into the respective lumens of the medical device 25, the guidewire loader apparatus may be removed from the end of the medical device 25. By applying an inward force to the opposed grip portions 52', 52" of the clip members 50', 50", the corresponding clip portions 53', 53" are spread apart in the clam-shell movement about the corresponding hinge sections 51', 51" at the base portion 33b. Once the corresponding tings 56', 56" move beyond the corresponding shoulder portions 57' 57", the first member 26a and the second member 26b are released from one another. Again, this design is particularly useful since removal of the members need not require stringing the loader all the way down the guidewire 21 to a proximal end thereof.

In an alternative embodiment (not shown), in an effort to align the second lumen opening 43 of the medical device with the second interface portion 46a and the second guidewire receiving portion 45a, an alignment tube may be added having a lumen suitably sized for sliding receipt of the second guidewire, yet having an outer diameter sized for receipt in the second lumen opening 43 of the medical device 25, as well as receipt in the second guidewire receiving portion 45.

In accordance with this alternative embodiment, a distal end of an alignment tube may be slideably pre-installed into the second lumen opening 43 of the medical device. During loading of the medical device 25 into the device receiving portion 27a, the alignment tube can be aligned with and placed into the second guidewire receiving portion 45. Once the first and second members are assembled, in the second position, the lumen of the alignment tube can be employed to facilitate insertion of the guidewire into the second guidewire lumen of the medical device. Subsequently, the alignment tube may be removed along with the loader apparatus.

Such a technique may be particularly useful for loading the second guidewire in bifurcation stent crimped onto a delivery catheter. In some designs, the guidewire is directed through the scaffolding of the crimped stent, and into the second lumen opening 43 of the medical device 25. During positioning on the loader, the crimped stent may move or be repositioned, blocking or impeding access to the second lumen opening.

Further still, it is contemplated that the guidewire loader in accordance with the present invention may be packaged together with a suitable medical device, such as that shown in U.S. Pat. No. 6,136,010, the entirety of which is hereby incorporated by reference. The guidewire loader may be disposed on the distal end of the medical device prior to packaging and sterilization, or the guidewire loader can be included in the packaging with the medical device prior to sterilization.

While the preferred embodiment of the invention has been illustrated and described, it will be appreciated that various changes can be made therein without departing from the scope of the invention. For example, a guidewire loading tool could have a conventional handle or a handle with a differently shaped ergonomic grip. It is therefore intended that the scope of the invention be determined from the following claims and equivalents thereof.

What is claimed is:

1. A guidewire loader apparatus for loading one or more guidewires into a plurality of guidewire lumens of a catheter comprising:
   a first member defining a respective catheter receiving portion having a first lumen diameter and a plurality of respective non-coaxial guidewire receiving portions in communication therewith at a respective interface portion having a lumen diameter substantially identical to the first lumen diameter; and
   a second member configured for placement in an opposed relationship to said first member, said second member defining a respective catheter receiving portion having lumen openings and a plurality of respective non-coaxial guidewire receiving portions in communication therewith at a respective interface portion, said first member and said second member cooperatively clamped together by mirror image clips on opposite sides of the first and second members, between a first position, enabling positioning of a catheter into the catheter receiving portion, and a second position, wherein the catheter receiving portion cooperates to align and support said catheter in a manner placing the lumen openings thereof substantially adjacent the cooperating, respective interface portions to permit aligned sliding receipt of respective ends of the guidewire into the cooperating, respective guidewire receiving portions, through the cooperating, respective interface portions and into the lumen openings of the catheter.

2. The guidewire loader apparatus according to claim 1, wherein each respective guidewire receiving portion is semi-conical-shaped, tapering inwardly toward the respective interface portion.

3. The guidewire loader apparatus according to claim 2, wherein each respective catheter receiving portion is semi-cylindrical-shaped.

4. The guidewire loader apparatus according to claim 1, wherein each the first member and the second member includes a respective base portion, configured for placement in an opposed relationship to one another, each respective base portion defining the respective catheter receiving portion, the guidewire receiving portion and the interface portion, and opposed, mirror image, respective manipulating tabs to enable manual operation between the first position and the second position.

5. The guidewire loader apparatus according to claim 4, wherein the respective manipulating tab of said first member extends from said respective base portion in a direction generally parallel to a longitudinal axis of the respective catheter receiving portion.

6. The guidewire loader apparatus according to claim 4, wherein, each respective manipulating tab is configured for placement in opposed relationship to one another on opposite sides of the first and second members.

7. The guidewire loader apparatus according to claim 4, wherein said manipulating tab of the second member includes a pair of opposed clip members hingeably mounted to the respective base portion on opposed sides of a longitudinal axis of the respective catheter receiving portion, one end of each clip member containing a respective grip portion, and an opposite end thereof containing a clip portion configured to releasably grip a corresponding clip region of the first member when the loader apparatus is in the second position.

8. The guidewire loader apparatus according to claim 7, wherein each respective clip portion of the corresponding clip member of the second member includes a ting, and each said clip region of the first member includes a shoulder portion that cooperates with a respective ting to releasably retain the second member and the first member together in the second position.

9. The guidewire loader apparatus according to claim 1, wherein, said second member includes a transparent material.

10. The guidewire loader apparatus according to claim 1, wherein said catheter receiving portion, said plurality of guidewire receiving portions, and said interface portion include smooth interiors without a stepped transition.

11. The guidewire loader apparatus according to claim 1, wherein each said first member and said second member having a substantially planar engaging face in opposed relationship with one another in the second position, each said engaging face defining the respective catheter receiving portion, the guidewire receiving portion and the interface portion.

12. The guidewire loader apparatus according to claim 11, further including: an alignment structure cooperating between the first member and the second member to align the respective catheter receiving portions, the guidewire receiving portions and the interface portions with one another in the second position.

13. The guidewire loader apparatus according to claim 12, wherein said alignment structure includes an alignment lip upstanding from one of the engaging faces, and peripherally surrounding at least a portion of the respective catheter receiving portion, the guidewire receiving portion and the interface portion, and a corresponding alignment recess downstanding from the other of the engaging faces, and peripherally surrounding the other of the at least a portion of the respective catheter receiving portion, the guidewire receiving portion and the interface portion.

* * * * *

UNITED STATES PATENT AND TRADEMARK OFFICE
CERTIFICATE OF CORRECTION

| | | |
|---|---|---|
| PATENT NO. | : 7,951,092 B2 | Page 1 of 1 |
| APPLICATION NO. | : 11/418692 | |
| DATED | : May 31, 2011 | |
| INVENTOR(S) | : Jones et al. | |

It is certified that error appears in the above-identified patent and that said Letters Patent is hereby corrected as shown below:

Column 2, line 50, after "from" delete "an" and insert instead --a--.

Column 5, line 24, after "handling" delete "or" and insert instead --of--.

Column 6, line 17, after "match" insert --the--.

Column 6, line 42, after "could" delete "includes" and insert instead --include--.

Column 8, line 13, after "28a" delete "28xb" and insert instead --28b--.

Column 12, line 36, after "including" delete ":".

Signed and Sealed this
Tenth Day of April, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,951,092 B2 | |
| APPLICATION NO. | : 11/418692 | |
| DATED | : May 31, 2011 | |
| INVENTOR(S) | : Andrew Jones et al. | |

It is certified that error appears in the above-identified patent and that said Letters Patent is hereby corrected as shown below:

On the Title page, Item (73), Assignee, delete "Abbott Cardiovascular Systems Inc." and insert instead --Abbott Laboratories--.

Signed and Sealed this
Third Day of July, 2012

David J. Kappos
*Director of the United States Patent and Trademark Office*